United States Patent [19]

Dickakian

[11] Patent Number: 4,752,587

[45] Date of Patent: * Jun. 21, 1988

[54] CHROMATOGRAPHIC METHOD FOR DETERMINING FOULING TENDENCY OF LIQUID HYDROCARBONS

[75] Inventor: Ghazi B. Dickakian, Kingwood, Tex.

[73] Assignee: Exxon Chemical Patents Inc., Linden, N.J.

[*] Notice: The portion of the term of this patent subsequent to Jun. 14, 2005 has been disclaimed.

[21] Appl. No.: 830,386

[22] Filed: Feb. 18, 1986

Related U.S. Application Data

[63] Continuation-in-part of Ser. No. 723,598, Apr. 15, 1985.

[51] Int. Cl.$^4$ .............................................. G01N 30/90
[52] U.S. Cl. ................... 436/60; 73/61.1 C; 73/61.2; 208/48 AA; 208/309; 436/139; 436/162
[58] Field of Search ................ 436/161, 162, 139, 60; 208/48 AA, 309; 73/61.2, 64, 61 R, 54, 61.1 C

[56] References Cited

U.S. PATENT DOCUMENTS

| | | | |
|---|---|---|---|
| 1,756,981 | 5/1930 | Jurrissen | 208/309 X |
| 2,196,989 | 4/1940 | Henry et al. | 208/309 X |
| 2,927,078 | 3/1960 | Nathan | 208/48 AA X |
| 2,981,684 | 4/1961 | Barnes | 208/48 AA X |
| 3,049,964 | 8/1962 | Miller et al. | 73/64 UX |
| 3,776,835 | 12/1973 | Dvoracek | 208/48 AA |
| 4,440,625 | 4/1984 | Go et al. | 208/48 AA |

FOREIGN PATENT DOCUMENTS 455272  4/1975  U.S.S.R. .................................. 73/64

OTHER PUBLICATIONS

Poirier et al., Chemical Abstracts, vol. 100, 1983, No. 100:36717m.
Poirier et al, Energy Sources, vol. 7, No. 2, pp. 165–176, 1983.
Touchstone et al, "Practice of Thin Layer Chromatography", published by John Wiley & Sons, New York, pp. 135–141, 1978.

*Primary Examiner*—Barry S. Richman
*Assistant Examiner*—Robert J. Hill, Jr.
*Attorney, Agent, or Firm*—R. L. Graham; J. F. Hunt

[57] ABSTRACT

A method for determining the fouling tendency of an asphaltene containing petroleum stream such as crude oil by the use of thin layer chromatography. The chromatogram of a crude oil formed in the presence of an asphaltene antisolvent which exhibits a fouling tendency developed a distinct, dark ring or disk.

18 Claims, 1 Drawing Sheet

WITHOUT ANTISOLVENT

WITH ANTISOLVENT (N-HEPTANE)

CHROMATOGRAPHIC METHOD FOR DETERMINING FOULING TENDENCY OF LIQUID HYDROCARBONS

This application is a continuation-in-part of Ser. No. 723,598 filed Apr. 15, 1985.

BACKGROUND OF THE INVENTION

1. Field of the Invention

The present invention relates to a chromatographic test method for determining the tendency of liquid hydrocarbon streams to foul equipment and more particularly to a method for determining oil-asphaltenes incompatibility and related fouling tendency. More specifically it is an improvement in a thin layer chromatographic method for determining the fouling tendency of said hydrocarbon streams.

2. Related Art

Different asphaltenes containing petroleum streams have different precipitating and fouling characteristics with regard to heated oil refinery surfaces. The problem of predicting the offending substances in a particular stream such as crude oil which foul heat exchanger equipment in oil refineries and petrochemical plants has been virtually unresolved. Equipment fouling by heated hydrocarbon streams which result in inorganic and carbonaceous deposits on heat exchanger surfaces leads to a blockage of flow and a decrease in heat transfer. Both resulting conditions severely reduce heat efficiency in the processing of the crude oil. If it can be predicted which crude oils or other petroleum streams are troublesome, measures can be taken in advance to prevent this fouling by either removing the offending substances causing the deleterious deposits, or by adding antifouling additives to the flow stream to reduce deposit formation. Therefore, it would be most desirable to be able to predict these streams with fouling tendencies.

There are a number of methods available for determining the rates of fouling of petroleum streams. Conceptually, they are all similar in that they attempt to measure the change in heat transfer from a heated surface to a test fluid.

One approach is to use a test unit which is configured to allow measurement of the fluid temperature at the exit of the heat-exchanger while the metal temperature of the heated tube is controlled. This configuration provides for close simulation of refinery and petrochemical plant heat-exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature while measuring the change in the liquid outlet temperature. As fouling progresses, i.e., a carbonaceous deposit build up on the heater tube surface, a decrease in the fluid outlet temperature results when using a constant outlet liquid temperature operation. The change in liquid outlet temperature with time provides the basic heat data required for comparative evaluation of untreated material and additive-treated material. The rate of change in outlet liquid temperature versus time shows relative fouling tendencies.

Current test equipment is only capable of measuring the overall tendency of heated petroleum streams to foul refinery equipment and cannot predict which are the offending substances or fractions.

In copending, commonly owned application U.S. Ser. No. 723,598 filed on 4/15/85, a chromatographic method for characterizing crude oil fouling was described which used thin layer chromatography (TLC). In some chromatograms the separation and difference in the asphaltenes and oil color is not visually clear. For those who are not familiar with TLC it maybe difficult to translate the poorly visual separation into fouling. In these cases, the asphaltene is not fully incompatible in the oil leading to the migration of some of the low molecular weight part of the asphaltenes with the oil and thus causing discoloration of the oil part. An improved method was therefore needed to clarify and simplify the interpretation and translation of the TLC chromatographic data into fouling characteristics.

Hence, it is an advantage of the present invention that an improved method which will predict the fouling tendency of asphaltene containing petroleum streams is provided. It is a particular advantage that the present invention (test) can be carried out in the refinery in a very short period of time by unit operators without extensive chemical training. It is a particular feature of the present invention that the visual demarcation line of the asphaltenes, if any is sharp and clear. These and other advantages and features will be apparent from the following text.

SUMMARY OF INVENTION

Briefly the present invention relates to a method which gives very clear chromatograms using an antisolvent to enhance the asphaltenes separation and thus producing clear chromatograms easy to translate into fouling. The modified TLC method is simple and can be used readily on-site in the refinery.

In some circumstances, it is useful to enhance the TLC separation of the asphaltenes from the oil fractions. This can be accomplished, for example, by dilution of the test sample of the petroleum stream with a paraffinic solvent (asphaltene antisolvent) such as n-heptane, iso-octane and hexane or a solvent containing polar atoms such as alcohols, ketones, amines, ethers, etc. The dilution with antisolvent can be varied from 1 to 3,000 percent based on the weight of the test sample.

Present invention is a method for determining the tendency of a liquid petroleum stream containing asphaltenes to foul refinery equipment comprising the steps of:

depositing a sample amount (usually one drop) of liquid petroleum from said stream onto the surface of a thin film having the property of chromatographic separation in the presence of an asphaltene antisolvent;

providing sufficient time for outward migration within said film of said amount; and determining the presence of an asphaltene ring in the thin film whereby the petroleum-asphaltenes incompatibility is evidenced.

There are two convenient means of obtaining the concurrent deposition of the antisolvent and feed sample onto the thin film. One method is to saturate the thin film of chromatographic material with the antisolvent prior to adding the feed sample. A second method comprises depositing a small amount (usually one drop) of a mixture of liquid petroleum from said stream and antisolvent onto a dry surface of a thin film having the property of chromatographic separation.

Thus, there has been discovered an effective, simple, inexpensive tool for visually identifying the fouling tendency of asphaltene containing liquid petroleum streams. This discovery is based on a recognition of the asphaltenes-oil enhanced incompatibility of petroleum streams in the presence of asphaltene antisolvent.

The utility of this discovery is demonstrated according to this invention by the use of thin layer chromatography as a means to determine the incompatibility of the high molecular weight asphaltene and oil fractions of the petroleum stream. The term "petroleum" as used herein includes crude oils, residual oils, hydrocarbons, heteroatom compounds normally found as constituents in crude oils and the fractions derived from any of the above.

Thus, there is provided a method for determining the tendency of oil containing asphaltenes to foul refinery equipment comprising the step of chromatographically separating said oil within a medium in the presence of antisolvent into respective deasphaltenated oil fraction and asphaltenes, whereby said tendency of said crude oil to foul said refinery equipment is visually indicated by a distinct demarcation between light fractions and said asphaltenes fraction.

The preferred antisolvents are low molecular weight, low viscosity paraffinic hydrocarbons and solvents containing polar atoms such as oxygen, nitrogen, chlorine and sulfur which are low boiling under the conditions of use (generally ambient temperatures). The antisolvent may be a single compound or a mixture of materials, i.e., one or more paraffins, polar solvents or mixtures thereof. The ambient temperature will vary with location and season, however, the testing will probably be carried out under temperature conditions no more sever than 0°-60° C. Generally the paraffinic hydrocarbons will contain from five to ten carbon atoms and suitably polar solvents would generally contain about this same number of carbon atoms (5 to 10 carbon atoms). It is to be appreciated that materials which fall outside of these general guide lines yet are antisolvents which when employed as described herein provide the improvement in visual separation of asphaltenes as described are within the broad scope of the present invention.

Once the petroleum stream has been identified as fouling according to the present invention, it is desirable to reduce fouling by incorporating a small quantity of an antifouling agent, such as the well known dispersants used in the refining industry, into the petroleum stream. Thus one aspect of the present invention is a method for reducing the fouling tendency of petroluem streams flowing through a vessel comprising;

(1) depositing a sample amount of liquid petroleum on to the surface of a thin film having the property of chromatographic separation in the presence of asphaltene antisolvent, (2) providing sufficient time for outward migration of said sample within said film, (3) determining the the presence of an asphaltenes ring in the thin film, and (4) thereafter adding at least an antifouling amount of an antifouling agent to said stream whereby its tendency to foul is reduced.

DETAILED DESCRIPTION OF THE INVENTION

Figure 1:
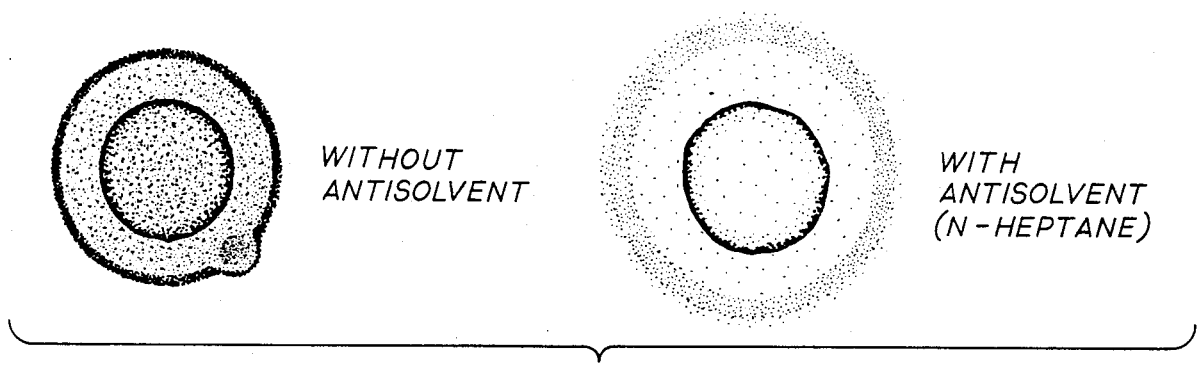
FIG. 1 illustrates TLC chromatograms of a high fouling crude oil with and without paraffinic antisolvent.

Petoleum streams used in refinery operations, in particular, crude oils, are composed of two major parts; high molecular weight asphaltene (fraction insolubles in paraffinic solvents) and a lower molecular weight asphaltene-free oil. The asphaltene and the oil fractions vary significantly in their chemical structure, coking characteristics, thermal characteristics, average molecular weight and distribution. The following Table 1 illustrates the varying differences in the characteristics of a typical heavy hydrocarbon, its asphaltene and oil fractions:

TABLE 1

|  | Total Hydrocarbons | Oil | C7 Asphaltenes |
|---|---|---|---|
| Aromatic Rings | 3 to 7+ | 3,4,5 | 7+ |
| Avg. mol. wt. | 250 | 190 | 1000 |
| Coking yield (wt %) | 8 | 3 | 65 |
| Aromatic carbon (% atom) | 65 | 60 | 69 |
| Carbon hydrogen atomic ratio | 0.97 | 0.90 | 1.19 |
| Melting point (°C.) | liquid | liquid | 190 |

Asphaltenes present in heavy hydrocarbons have high molecular weight and very broad molecular distribution, sometimes with molecular weights up to 10,000.

Generally speaking, the present invention uses thin layer chromatography (TLC), enhanced by the presence of the antisolvent, to separate, e.g. by adsorption, the high molecular weight asphaltenes and the low molecular weight oil fractions. Thin layer chromatography is a well known technique as described in a book by Joseph C. Touchstone and M. F. Dobbins, entitled: "Practice of Thin Layer Chromatography," published by Wiley-Interscience, 1978.

Thin layer chromatography is a separation method in which uniform thin layers of selected sorbent media are used as a carrier medium. The sorbent is applied to a backing as a coating to obtain a stable layer of suitable size. The most common support is a glass plate, but other supports such as plastic sheets and aluminum foil are also used. The four sorbents most commonly used are silica gel, alumina, kieselguhr (diatomaceous earth), and cellulose. Silica gel (silicic acid) is the most popular material. It is slightly acidic in nature. In order to hold the silica gel firmly on the support, a binding agent such as plaster of paris (calcium sulfate hemihydrate) is commonly used. With many crudes separation can be accomplished in less than an hour at a very reasonable cost.

Fouling tendencies of the petroleum oil are indicated in the chromatographic medium by extreme differences in the migration of the molecularly light and heavy fractions. These differences are shown by a clear demarcation between visually light and dark areas. Where heavy asphaltene fractions are incompatible with the lighter matrix oil, a distinct dark colored ring or disk is formed as a result of the outward migration of the oil from the point of its deposition onto the chromatographic medium.

The invention features a method for predicating the fouling tendency of a crude oil to foul refinery equipment using the TLC techniques with a specific absorbent medium and antisolvent.

The crude oil is separated in a thin sorbent medium into respective molecularly light and heavy (asphaltenes) fractions, which are characterized by visually light and dark areas within the medium. The tendency of the crude oil to cause fouling in the refinery equipment is indicated by a visually distinct demarcation between the light and dark areas which dark area appears as a ring or disk.

A drop from the petroleum stream on to the thin layer chromatographic medium, either in admixture with asphaltene antisolvent or with asphaltene antisolvent saturated into the medium, is fractionated by allowing the various fractions to migrate for a time sufficient to produce distinct demarcations between them. As previously discussed, the formation of a dark brown or black ring in the center of the medium will indicate the presence of incompatible high molecular weight asphaltenes which will have a tendency to cause fouling in conventional oil refinery operations.

Currently used methods, procedures and equipment are only capable of measuring the overall tendency of crude oils to foul refinery equipment, and cannot predict which offending substances or fractions are responsible for fouling. Such current test equipment accelerates the heat conditions leading to precipitation of carbonaceous deposits, without analyzing which fractions of the crude oil are responsible for the fouling. The use of thin layer chromatography to separate the fractions of various fouling and non-fouling oils in the presence of antisolvent to identify the oil-asphaltene incompatibility provides a method capable of predicting by a quick and inexpensive test when a particular crude oil would foul the refinery equipment without the need for high temperature acceleration which should be avoided when possible as it produces fouling data which is not related to actual fouling in the refinery. This method of the invention can be corroborated by thereafter determining which oils have a tendency to cause fouling by the Thermal Fouling Tester (an apparatus widely used in the industry to measure the fouling tendencies of crude oils and hydrocarbon streams). Chromatograms of the various crude oils have been made, and the results of these chromatograms thereafter correlated to the known fouling characteristics of each crude oil.

All of the Examples cited herein demonstrating the predictability of the fouling characteristics of crude oils utilized the laboratory test apparatus known as the Thermal Fouling Tester for corroboration of the predictions.

The Tester is a modification of the Alcor Tester described in ASTM Vol. 50 D-3241. It is configured to allow measurement of the fluid temperature at the exit of the heat-exchanger while the metal temperature of the heated tube is controlled. The test thus measures the change in temperature of a fluid which has been pumped across a heated surface. The outlet temperature is directly related to the heat transferred to the fluid. If fouling occurs, a deposit adheres to the heated metal surface and insulates the surface from the test fluid. The insulating deposit reduces the rate of heat transfer to the fluid and its temperature decreases. The rate of change in the fluid temperature is a measure of the rate of fouling.

The time over which temperature measurements are recorded was set at 3 hours. By doing this, the changes in temperatures of several fluids can be used as a measure of their relative fouling tendencies.

As used herein, oil-asphaltene incompatibility of the total petroleum stream is indicative of the susceptibility of asphaltenes to separate from the oil, adhere to the heated metal surface, transfer into coke-like material and result in fouling of the metal surface. The greater the incompatibility of the asphaltenes in the oil; the higher the fouling tendency of the hydrocarbon stream.

Asphaltenes present in crude oils have high average molecular weight ($Mn=900-1300$) and a very broad molecular weight distribution. Gel permeation chromatographic (GPC) characterization of two crude oil asphaltenes molecules indicates the presence of molecular weight as high as 5000.

Paraffinic and polar solvents can be used and these are effective only over a broad range of oil/solvent ratios. These antisolvents must be of low molecular weight, low viscosity and have low boiling characteristics to allow rapid migration on the TLC chromatographic plate.

The paraffin antisolvents are preferably up to $C_{10}$ straight or branched alkanes, usually $C_5$ to $C_{10}$, e.g., suitable antisolvents include pentane, isopentane, hexane, 2-methyl hexane, n-heptane, octane, nonane, decane, isooctane and the like.

The polar antisolvents cover a broader spectrum of materials. The present polar solvents are organic compounds which are liquids under the conditions of use. The term "polar" refers to atoms such as oxygen, sulfur, oxygen halogens and nitrogen. A partial listing of suitable polar antisolvents includes alcohols such as, isobutanol, 2-pentanol, isoamyl alcohol; ketones such as acetone; methyl ethyl ketone; ethers such as diethyl ether, methyl propyl ether; esters such as methyl formate, butyl formate, methyl acetate, methyl propionate; glycol ethers, such as ethylene glycol monomethyl ether, ethylene glycol diethyl ether; heteroatom compounds such as furan, tetrahydrofuran, furfural, methyl pyridine, and the like. Mixtures of hydrocarbon and polar materials are desired antisolvents for petroleum streams containing functional groups. The selection of a suitable antisolvent depends on the atmospheric temperature of the TLC plate. For example, in the laboratory (20° C.) n-heptane was used satisfactorily. On-site testing in cold weather, may require pentane or isooctane, whereas a refinery site in hot weather such as in Texas or Louisiana where the TLC glass plate will have high temperature, may require a high boiling antisolvent such as nonane or decane.

The present method of fouling characterization is simple and easy to use in the laboratory and in the field for monitoring crude oil characteristics routinely by non technical personnel. The method may be used in two ways: (a) By the addition of the antisolvent to the crude oil, mixing the blend for few minutes, and then applying a drop of the oil/solvent blend onto a dry TLC plate. The TLC chromatogram will develop in a very short time. The ratio of antisolvent to oil will obviously vary from crude to crude, not only for the enhancement of the insolubility of the asphaltenes but also to reduce the viscosity of the crude to an extent to make it operable with the TLC chromatographic plate. Light and medium crudes require only a few minutes for development of the chromatographic pattern, whereas heavy crudes, such as the California crudes, may require a few hours.

The antisolvent is preferably added to the oil in a weight ratio ranging from 0.2:1 to 1:0.2, more preferably 0.5:1 to 1:0.5 (antisolvent:oil ratio). The use of the correct oil/antisolvent ratio is important for the successful separation of asphaltene and oil on the TLC plate. When adding the antisolvent to the oil, the antisolvent will insolubilize the asphaltene, especially the low molecular weight part of the asphaltenes and produce a very clear and well defined asphaltene ring on the TLC plate, which can then be easily related to fouling characteristics with greater assurance by the unit operator using the test.

(b) The present method can also be used by simply adding a few drops of the antisolvent onto the dry TLC plate (just to wet the thin film) and then applying a drop of the oil onto the wet film and allowing the chromatogram to develop. This method is particularly suitable for on-site tests in the refinery. It is also possible to use a combination of the two embodiments of the present invention, which may be useful with very heavy crudes.

The following procedure was used in examples 1-6 to produce the several thin layer chromatograms:

A 10×10 cm silica gel coated glass plate was used. A drop of the crude oil or the fraction was dropped gently on the plate saturated with n-heptane, isopropyl alcohol, acetone or tetrahydrofuran. The covered plate was allowed to stand at room temperature on a flat surface for one hour For light crude oils employed in the following examples the separation was completed in a few minutes. Unless specified otherwise, all parts and percentages herein are by weight.

EXAMPLE 1

A high fouling crude oil, Crude #1 was subjected to chromatographic separation on a silica-gel TLC plate saturated with antisolvent n-heptane at room temperature. After about one minute the plate exhibited the respective chromatograms illustrated in FIG. 1 showing clearly the incompatible asphaltene ring. The plate was allowed to stand for one hour for complete development of the chromatogram.

For comparison purposes, FIG. 1 also presents a TLC chromatogram of Crude oil #1 without the use of the antisolvent n-heptane.

EXAMPLE 2

A sample of high fouling crude oil, Crude #2 was subjected to chromatographic separation on a silica gel TLC plate saturated with antisolvent n-heptane. After about an hour the asphaltene separation occurred as illustrated in FIG. 2.

Figure 2:
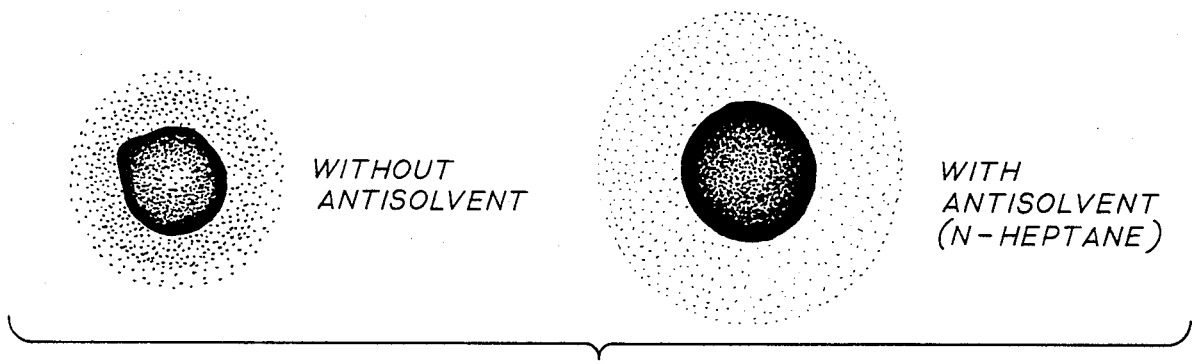
FIG. 2 illustrated TLC chromatograms of a second high fouling crude oil with and without paraffinic antisolvent.

For comparison purposes, FIG. 2 also illustrated the TLC chromatogram of Crude oil #2 without the use of n-heptane.

EXAMPLE 3

A sample of high fouling crude oil, Crude #3 was subjected to chromatographic separation on a TLC plate saturated with antisolvent (n-heptane). The plate was allowed to stand at room temperature for one hour. The chromatogram showed very clearly the presence of the incompatible asphaltenes which is illustrated in FIG. 3.

Figure 3:
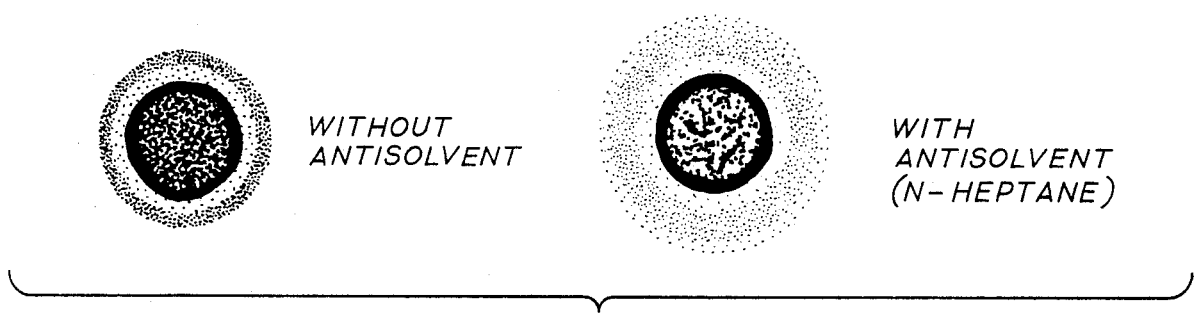
FIG. 3 illustrates TLC chromatograms of a third high fouling crude oil with and without paraffinic antisolvent.

For comparison purposes, FIG. 3, also illustrates the TLC chromatogram of Crude #3 without the use of antisolvent.

EXAMPLE 4

A sample of high fouling crude oil, (Crude #2) was subjected to TLC chromatographic separation on TLC plate saturated with antisolvent acetone. The chromatogram (FIG. 4) clearly shows the presence of incompatible asphaltenes as a dark ring which is indicative of high fouling characteristics.

EXAMPLE 5

Figures 4, 5, 6:
FIG. 4 illustrates a TLC chromatogram of the crude oil of FIG. 2 with a polar antisolvent (acetone).
FIG. 5 illustrates a TLC chromatogram of the crude oil of FIG. 2 with a second polar antisolvent (isopropyl alcohol).
FIG. 6 illustrates a TLC chromatogram of the crude oil of FIG. 2 with a third polar antisolvent (tetrahydrofuran).

A sample of high fouling crude oil (Crude #2) was subjected to TLC chromatographic separation using isopropyl alcohol as antisolvent. The TLC chromatogram clearly shows the presence of the incompatible asphaltenes (FIG. 5).

EXAMPLE 6

A sample of high fouling crude oil (Crude #2) was subjected to TLC chromatographic separation using tetrahydrofuran as antisolvent. The TLC chromatogram shows the presence of a dark color asphaltene in the center of the chromatogram which is a clear indication of high fouling characteristics.

EXAMPLES 7, 8 and 9

Fouling Measurement of Various Crude Oils by the Thermal Fouling Tester

The Thermal Fouling Tester was used to determine the fouling characteristics of the 3 crude oils used in the present examples. The test measures the change in temperature ($\Delta T$, °F.) between 0 time and 180 minutes. $\Delta T$ of 1°-10° F. is low fouling, 20°-30° F. is medium fouling and 45+° F. is high fouling.

Thermal Fouling Unit tests were carried out for 180 minutes at the following operating conditions:
Tube Temperature=371° C.
Nitrogen pressure=500 psig
Crude Flow=3.0 ml./min.
Preheat time to 371° C.=20 min.
Inner heat tube=Reconditioned (Carbon/Steel)

A summary of the fouling characteristics ($\Delta T$, °F.) of the several hydrocarbon types is presented in Table II below

TABLE II

| Example # | Hydrocarbon Type | Fouling ($\Delta T$, °F.) |
|---|---|---|
| 7 | Crude #1 | 59 |
| 8 | Crude #2 | 62 |
| 9 | Crude #3 | 52 |

The Thermal Fouling Tester (TFT) results presented in the above table gives the fouling characteristics of the various hydrocarbon streams TFT data confirms the fouling tendencies or lack thereof of various hydrocarbon streams as predicted by the method of this invention.

It will be further understood that the present invention is not necessarily limited to the above-described embodiments, but rather is subject to variations and modifications without departing from its broader aspects.

The step of determining oil-asphaltenes incompatibility in a preferred embodiment as demonstrated by the examples may be performed visually. However, it is intended that the scope of this invention covers instrumental means for determining such incompatibilities. Specific examples include (a) light scanning devices for detecting differential color intensity between the asphaltenes and oil, (b) light transmission differential between the asphaltenes and oil, (c) detectible differential responses when using other sources such as infrared light, ultraviolet light, lazer sources, radiation sources, etc.

The invention claimed is:

1. A method for determining the tendenacy of a liquid hydrocarbon stream to foul equipment comprising the steps of:
   (a) depositing a sample of liquid hydrocarbon from a liquid hydrocarbon stream onto a surface of a thin film in the presence of an asphaltene antisolvent, wherein the thin film is made up of a chromatographic separation material;
   (b) letting the sample of liquid hydrocarbon migrate radially outward within said film for sufficient time so that hydrocarbon compatible fractions in the sample separate from any hydrocarbon-incompatible asphaltenes in the sample, wherein said hydrocarbon compatible fractions form a matrix portion in the film and any hydrocarbon-incompatible asphaltenes form a dark ring within the matrix portion and wherein any ring formed is disposed within a central region of the matrix portion and is distinguished from the matrix portion by a dark area having a boundary with respect to a lighter area; and
   (c) determining the tendency of the liquid hydrocarbon stream to foul equipment by comparing the matrix portion with any dark ring formed from any hydrocarbon-incompatible asphaltenes in the sample, wherein the area and intensity of any ring formed in relation to the matrix portion provides an indication of the tendency of the liquid hydrocarbon stream to foul equipment.

2. The method according to claim 1 wherein the chromatographic separation material is such that hydrocarbon compatible fractions and any hydrocarbon-incompatible asphaltenes in said sample separate from the sample in step (b) by adsorption.

3. The method according to claim 1, wherein the chromatographic separation material is a finely divided thin layer chromatographic separation material and is such that hydrocarbon compatible fractions and any hydrocarbon-incompatible asphaltenes in said sample separate from the sample is step (b) by adsorption.

4. The method according to claim 1, wherein the chromatographic separation material is selected from the group consisting of acidic silica gel, alumina, and kieselguhr.

5. The method according to claim 1, wherein the antisolvent is a liquid while the method steps are carried out and is selected from the group consisting of lower paraffinic hydrocarbons, polar solvents, and mixtures thereof.

6. The method according to claim 5, wherein an amount of the antisolvent and the sample are admixed prior to depositing the sample onto the surface of the thin film.

7. The method according to claim 6 wherein the amount of antisolvent admixed with the sample is from 1 to 3,000 percent by weight based on the weight of the sample.

8. The method according to claim 5 wherein the antisolvent is applied to the thin film prior to depositing the sample on the surface of the thin film.

9. The method according to claim 8, wherein the antisolvent is a polar solvent having five to ten carbon atoms and containing oxygen, sulfur, notrogen, or halogen atoms.

10. The method according to claim 8, wherein the antisolvent is a polar compound selected from the group consisting of acetone, isopropyl alcohol, and tetrahydrofuran.

11. The method according to claim 8, wherein said antisolvent is a paraffinic hydrocarbon having five to ten carbon atoms.

12. The method according to claim 11, wherein said antisolvent is n-heptane.

13. The method according to claim 5, wherein the antisolvent and the sample are admixed in a weight ratio of antisolvent: sample in the range of 0.21:1 to 1:0.2.

14. The method according to claim 13 wherein the weight ratio of antisolvent: sample is in the range of 0.5:1 to 1:0.5.

15. The method according to claim 14 wherein the antisolvent is a paraffinic hydrocarbon having five to ten carbon atoms.

16. The method according to claim 14 wherein the antisolvent is a polar solvent having five to ten carbon atoms and containing oxygen, sulfur, nitrogen, or halogen atoms.

17. The method according to claim 14, wherein the antisolvent is a polar compound selected from the group consisting of acetone, isopropyl alcohol, and tetrahydrofuran.

18. A method for reducing the fouling tendency of a hydrocarbon stream flowing through a vessel comprising the steps of:
   (a) carrying out the method of claim 1; and
   (b) based on the determination of the tendency of the liquid hydrocarbon stream to foul equipment and in response thereto, adding at least an antifouling amount of an antifouling agent to said agent to reduce its tendency to foul.

* * * * *